United States Patent [19]

Sorg et al.

[11] 4,337,198
[45] Jun. 29, 1982

[54] PYRAZINOBENZODIAZEPINES

[75] Inventors: Dieter Sorg, Bern; Albert Leutwiler, Hinterkappelen, both of Switzerland

[73] Assignee: Sandoz Ltd., Basel, Switzerland

[21] Appl. No.: 143,263

[22] Filed: Apr. 24, 1980

[30] Foreign Application Priority Data

May 11, 1979 [CH] Switzerland ............... 4418/79

[51] Int. Cl.³ ............... C07D 487/02; A61K 31/495
[52] U.S. Cl. ............... 260/243.3; 424/250
[58] Field of Search ............... 260/243.3

[56] References Cited

U.S. PATENT DOCUMENTS 3,458,516 7/1969 Howell et al. ............... 200/243.3
3,917,585 11/1975 Bebenburg ............... 260/243.3

OTHER PUBLICATIONS

Schmutz Arzheim-Forsch, 25, pp. 712-720, (1975).

Primary Examiner—David B. Springer
Attorney, Agent, or Firm—Gerald D. Sharkin; Robert S. Honor; Joseph J. Borovian

[57] ABSTRACT

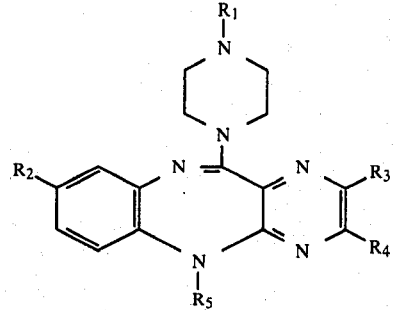

wherein
$R_1$ is hydrogen, alkyl of 1 to 4 carbon atoms, hydroxyalkyl with a maximum of 4 carbon atoms, the hydroxy group of which may be acylated by an alkanoyl group of 2 to 18 carbon atoms, alkoxyalkyl with a maximum of 6 carbon atoms, cycloalkyl of 3 to 6 carbon atoms, cycloalkylalkyl of 4 to 7 carbon atoms, or a group of formula II,

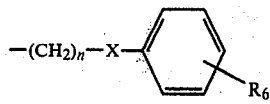

wherein
$R_6$ is hydrogen, halogen, or alkyl or alkoxy of 1 to 4 carbon atoms, and
either
(i) X is —CH$_2$— and n is 0, 1, 2 or 3 or
(ii) X is —CO— and n is 1, 2 or 3 or
(iii) X is —O— and n is 2 or 3,
$R_2$ is hydrogen, halogen, trifluoromethyl or alkyl of 1 to 4 carbon atoms,
$R_3$ is hydrogen, halogen, trifluoromethyl, or alkyl or alkoxy of 1 to 4 carbon atoms,
$R_4$ is hydrogen, or alkyl or alkoxy of 1 to 4 carbon atoms,
and
$R_5$ is hydrogen, alkyl of 1 to 4 carbon atoms or alkenyl of 3 or 4 carbon atoms, with the proviso that, when $R_2$ is hydrogen, $R_5$ is hydrogen,
are useful for inducing sleep and treating psychoses and depressions.

25 Claims, No Drawings

PYRAZINOBENZODIAZEPINES

The present invention relates to pyrazinobenzodiazepines, processes for their production and pharmaceutical compositions containing them.

The present invention provides compounds of formula I,

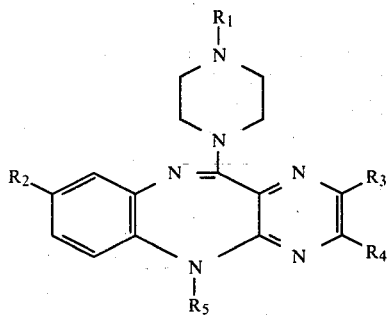

wherein
$R_1$ is hydrogen, alkyl of 1 to 4 carbon atoms, hydroxyalkyl with a maximum of 4 carbon atoms, the hydroxy group of which may be acylated by an alkanoyl group of 2 to 18 carbon atoms, alkoxyalkyl with a maximum of 6 carbon atoms, cycloalkyl of 3 to 6 carbon atoms, cycloalkylalkyl of 4 to 7 carbon atoms, or a group of formula II,

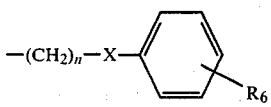

wherein
$R_6$ is hydrogen, halogen, or alkyl or alkoxy of 1 to 4 carbon atoms, and
either
(i) X is —$CH_2$— and n is 0, 1, 2 or 3 or
(ii) X is —CO— and n is 1, 2 or 3 or
(iii) X is —O— and n is 2 or 3,
$R_2$ is hydrogen, halogen, trifluoromethyl or alkyl of 1 to 4 carbon atoms,
$R_3$ is hydrogen, halogen, trifluoromethyl, or alkyl or alkoxy of 1 to 4 carbon atoms,
$R_4$ is hydrogen, or alkyl or alkoxy of 1 to 4 carbon atoms,
and
$R_5$ is hydrogen, alkyl of 1 to 4 carbon atoms or alkenyl of 3 or 4 carbon atoms, with the proviso that, when $R_2$ is hydrogen, $R_5$ is hydrogen.

Any alkyl or alkoxy radical of 1 to 4 carbon atoms is preferably of 1 to 3 carbon atoms, especially 1 and 2 carbon atoms. Hydroxyalkyl has preferably 2 or 3 carbon atoms and preferably the hydroxy group in free form or in acylated form is attached to a carbon atom other than the carbon atom adjacent to the nitrogen atom. The alkoxy moiety in alkoxyalkyl is preferably located in the terminal position of the alkylene chain which preferably has 2 or 3, especially 2, carbon atoms. The alkoxy radical in alkoxyalkyl is preferably methoxy. Cycloalkyl or the cycloalkyl moiety of cycloalkylalkyl is conveniently cyclopentyl and especially cyclopropyl. The alkyl moiety of cycloalkylalkyl has conveniently 1 carbon atom. Halogen means fluorine, chlorine, bromine or iodine. Halogen is conveniently fluorine, chlorine or bromine, preferably fluorine or chlorine, and especially chlorine. The double bond of alkenyl is preferably not in the $\alpha,\beta$-position.

$R_1$ is preferably hydrogen, alkyl, cycloalkylalkyl or a group of formula II and especially alkyl. $R_6$ is preferably hydrogen or halogen. X is conveniently —CO— and preferably —$CH_2$—. When X is —O—, n is preferably 3, or when X is —CO— or —$CH_2$—, n is preferably 1 or 3. $R_2$ is preferably hydrogen, halogen or alkoxy. $R_3$ is preferably hydrogen, halogen or alkyl. $R_4$ is preferably hydrogen.

The present invention also provides a process for the production of a compound of formula I as defined above, which comprises reacting a compound of formula III,

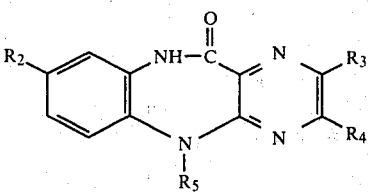

wherein $R_2$, $R_3$, $R_4$ and $R_5$ are defined above, with a metal amine complex comprising a metal of the group IVb of the periodic system, or vanadium, and a compound of formula IV,

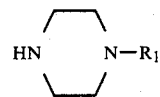

wherein $R_1$ is as defined above.

The reaction may be effected in conventional manner for the production of similar compounds. The reaction is conveniently carried out in the presence of an acid-binding agent. Acid-binding agents which may be used are tertiary amines, e.g. triethylamine, pyridine, dimethylaniline, or an excess of the compound of formula IV. Preferably titanium is used as the metal. Conveniently the complex is obtained from the metal tetrachloride.

The compounds of formula IIIa,

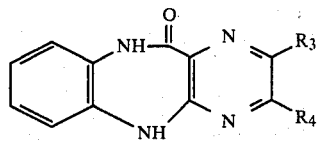

wherein $R_3$ and $R_4$ are as defined above, may be obtained for example by condensing compounds of formula V,

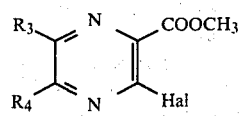

wherein $R_3$ and $R_4$ are as defined above, and Hal is bromine or chlorine, with 1,2-phenylene diamine.

The compounds of formula IIIb,

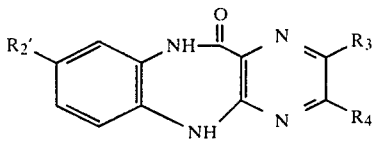

wherein $R_3$ and $R_4$ are as defined above, and $R_2'$ is halogen, trifluoromethyl or alkyl of 1 to 4 carbon atoms, may be obtained, for example, by cyclizing compounds of formula VI,

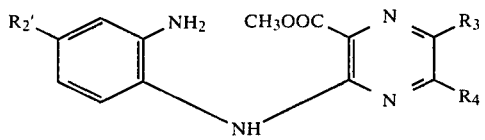

wherein $R_2'$, $R_3$ and $R_4$ are as defined above.

Compounds of formula VI may, for example, be obtained by reduction of compounds of formula VII,

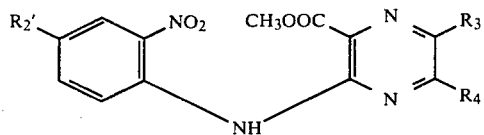

wherein $R_2'$, $R_3$ and $R_4$ are as defined above.

Compounds of formula VII may, for example, be obtained by mononitration of compounds of formula VIII,

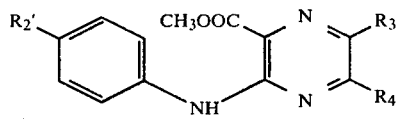

wherein $R_2'$, $R_3$ and $R_4$ are as defined above.

Compounds of formula VIII may, for example, be obtained by reacting compounds of formula V with compounds of formula IX,

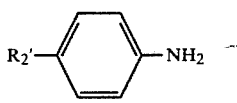

wherein $R_2'$ is as defined above.

Compounds of formula III, wherein $R_5$ is alkyl or alkenyl, and $R_2$ is halogen, trifluoromethyl or alkyl, and $R_3$ and $R_4$ are as defined above, may, for example, be prepared by alkylating or alkenylating compounds of formula VII, reducing the resulting N-alkyl- or N-alkenyl-derivatives and cyclising the resultant diamines.

Insofar as the production of any starting material is not particularly described, this may be effected in known manner or in analogous manner to the production of similar known compounds.

Free base forms of the compounds of formula I may be converted into acid addition salt forms in conventional manner and vice versa. Suitable acids are e.g. maleic acid, oxalic acid, methanesulphonic acid, hydrochloric acid and hydrobromic acid.

In the following Examples the temperatures given are in degrees Centigrade and are uncorrected.

In the table the following abbreviation is used: *) monomaleate.

EXAMPLE 1:
8-chloro-5-methyl-11-(4-methyl-piperazinyl)-pyrazino[2,3-b][1,5]benzodiazepine To an ice-cooled suspension of 3.0 g of 8-chloro-5-methyl-pyrazino[2,3-b][1,5]benzodiazepin-11(10H)-one in 100 ml absolute tetrahydrofuran and 6.2 ml N-methylpiperazine is added dropwise a solution of 1.8 ml titanium tetrachloride in 35 ml of absolute benzene. The mixture is stirred at room temperature for 30 minutes and then boiled at reflux for 2 hours. After the mixture has been cooled, 15 ml of water are added dropwise, the suspension is filtered and the residue washed with ethyl acetate. The filtrate is then evaporated and the residue treated with ethyl acetate and 4 N hydrochloric acid. The aqueous phase is made alkaline with sodium hydroxide and extracted with methylene chloride. The organic phase is evaporated to dryness to give the heading compound as an oil, which is crystallised and recrystallised from diisopropylether, m.p. 180°–182°.

The starting material 8-chloro-5-methyl-pyrazino[2,3-b][1,5]benzodiazepine-11(10H)-one may be obtained as follows:

(a) 3-(4-chlorophenylamino)-pyrazine-2-carboxylic acid methyl ester

A mixture of 21.7 g 3-bromo-pyrazine-2-carboxylic acid methyl ester and 25.5 g 4-chloroaniline in 150 ml ethyl acetate is boiled 4 days at reflux. The solution is washed with 4 N hydrochloric acid, water and then with 2 N sodium carbonate. The organic phase is dried over sodium sulphate and evaporated to give the heading compound (recrystallised from isopropanol) m.p. 135°–136°.

(b) 3-(4-chloro-2-nitrophenylamino)-pyrazine-2-carboxylic acid methyl ester

A suspension of 2.6 g 3-(4-chlorophenylamino)-pyrazine-2-carboxylic acid methyl ester in 100 ml nitromethane is stirred and treated dropwise at 0° C. with 24 ml nitric acid (99%). Stirring is continued at 0° C. for further 45 minutes. The solution is poured on ice and extracted with methylene chloride. The organic phase is washed with saturated sodium bicarbonate solution, dried over sodium sulphate and evaporated to give the heading compound, m.p. 191°–192°.

(c) 3-(4-chloro-N-methyl-2-nitrophenylamino)-pyrazine-2-carboxylic acid methyl ester A solution of 3.1 g 3-(4-chloro-2-nitrophenylamino)-pyrazine-2-carboxylic acid methyl ester in 15 ml absolute hexamethylphosphorotriamide is treated portionwise with 0.3 g sodium hydride. The reaction mixture is stirred at room temperature for 1 hour and then treated dropwise with 2.8 g methyl iodide, and the temperature is maintained under 20° C. After the reaction mixture has been stirred for 1 hour at room temperature 10 ml water are added dropwise. The mixture is extracted with ethyl acetate. The organic phase is washed with water, dried over sodium sulphate and evaporated. The residue is recrystallised from ethyl acetate to give the heading compound, m.p. 111°–112°.

(d) 3-(2-amino-4-chloro-N-methyl-phenylamino)-pyrazine-2-carboxylic acid methyl ester A mixture of 4.0 g 3-(4-chloro-N-methyl-2-nitrophenylamino)-pyrazine-2-carboxylic acid methyl ester, 200 ml ethyl acetate and 4 g Raney Nickel are hydrogenated at room temperature under normal pressure. The catalyst is removed by filtration and the filtrate is evaporated to afford the heading compound. It is used without further purification.

(e) 8-chloro-5-methyl-pyrazino[2,3-b][1,5]benzodiazepin-11(10H)-one

To a solution of 6.5 g 3-(2-amino-4-chloro-N-methyl-phenylamino)-pyrazine-2-carboxylic acid methyl ester in 100 ml N,N-dimethyl-formamide are added 5.0 g potassium tert. butylate at 0° C. The mixture is stirred at room temperature for 2 hours, poured into ice water and acidified to pH 4 with glacial acetic acid, whereupon the heading compound is precipitated, m.p. 305°–307° (recrystallised from methanol).

In analogous manner to that described in Example 1, the following compounds of formula I are obtained:

| Ex. | $R_1$ | $R_2$ | $R_3$ | $R_4$ | $R_5$ | m.p.[1] |
|---|---|---|---|---|---|---|
| 2 | H | H | H | H | H | 221–225 |
| 3 | CH$_2$CH$_2$—C$_6$H$_5$ | H | H | H | H | 175–176 |
| 4 | CH$_2$CH$_2$—C$_6$H$_4$Cl | H | H | H | H | 207–208 |
| 5 | CH$_2$—cyclopropyl | H | H | H | H | 204–205 |
| 6 | CH$_3$ | H | Cl | H | H | 188–190 |
| 7 | CH$_2$CH$_2$—C$_6$H$_5$ | H | Cl | H | H | 166–167 |
| 8 | CH$_2$CH$_2$—C$_6$H$_4$Cl | H | Cl | H | H | 149–150 |
| 9 | CH$_2$—cyclopropyl | H | Cl | H | H | 148 |
| 10 | CH$_3$ | Cl | H | H | H | 208–209 |
| 11 | CH$_2$CH$_2$—C$_6$H$_5$ | Cl | H | H | H | 170–172 |
| 12 | CH$_2$—cyclopropyl | Cl | H | H | H | 165–167 |
| 13 | CH$_3$ | F | H | H | CH$_3$ | 160–162 |
| 14 | H | F | H | H | CH$_3$ | 142–145* |
| 15 | CH$_3$ | Cl | Cl | H | H | 221–222 |
| 16 | CH$_3$ | F | H | H | H | 255–256 |
| 17 | CH$_3$ | H | H | H | H | 238 |
| 18 | H | Cl | H | H | CH$_3$ | 151–153* |
| 19 | CH$_3$ | H | H | CH$_3$ | H | 195–197* |
| 20 | CH$_3$ | Cl | H | CH$_3$ | H | 236–237* (decomp.) |
| 21 | CH$_3$ | Cl | Cl | CH$_3$ | H | 196–198 |
| 22 | CH$_3$ | Br | H | H | H | 202–203 |
| 23 | CH$_2$—cyclopropyl | F | H | H | CH$_3$ | |
| 24 | CH$_3$ | H | CH$_3$ | H | H | |
| 25 | H | Cl | Cl | H | H | |

*monomaleate
[1]free base except where otherwise stated

The starting materials of formula III for Examples 10–16, 20–23 and 25 are prepared in analogous manner to that described in Example 1, steps (a) to (e).

The starting material of formula III for Examples 2 to 5 and 17 may be obtained as follows:

2.2 g of 3-bromo-pyrazine-2-carboxylic acid methyl ester and 2.2 g 1,2-phenylene diamine suspended in 50 ml triethylamine are boiled for 17 hours under reflux. After the mixture has been cooled, water and ethyl acetate are added to precipitate out pyrazino [2,3-b][1,5]benzodiazepin-11(10H)-one, m.p. 298°–300°.

The starting materials of formula III for Examples 6 to 9, 19 and 24 may be obtained in analogous manner.

The following compounds of formula I may be made wherein $R_4$ is —O—n—$C_4H_9$ and $R_5$ is —CH$_2$—CH=CH—CH$_3$ and

| Ex. | $R_1$ | $R_2$ | $R_3$ |
|---|---|---|---|
| (a) | HOC$_2$H$_4$ | CF$_3$ | CF$_3$ |
| (b) | CH$_3$COOC$_2$H$_4$ | C$_2$H$_5$ | C$_2$H$_5$ |
| (c) | nC$_{10}$H$_{21}$CO—OC$_2$H$_4$ | C$_2$H$_5$ | OC$_2$H$_5$ |
| (d) | nC$_{18}$H$_{37}$CO—OC$_2$H$_4$ | C$_2$H$_5$ | OC$_2$H$_5$ |
| (e) | CH$_3$—O—C$_3$H$_6$ | C$_2$H$_5$ | OC$_2$H$_5$ |
| (f) | —CH$_2$—C$_6$H$_5$ (with C$_2$H$_5$ substituent) | C$_2$H$_5$ | OC$_2$H$_5$ |
| (g) | —(CH$_2$)$_3$—C$_6$H$_5$ | C$_2$H$_5$ | OC$_2$H$_5$ |
| (h) | —(CH$_2$)$_4$—C$_6$H$_5$ | C$_2$H$_5$ | OC$_2$H$_5$ |
| (i) | —(CH$_2$)$_n$—CO—C$_6$H$_5$, n = 1, 2 or 3 | C$_2$H$_5$ | OC$_2$H$_5$ |
| (j) | —(CH$_2$)$_n$—O—C$_6$H$_5$, n = 2 or 3 | C$_2$H$_5$ | OC$_2$H$_5$ |

The compounds of formula I are useful because they possess pharmacological activity in animals. In particular, the compounds of formula I are useful as neuroleptic agents in the treatment of e.g. psychotic disturbances, as indicated in standard tests, e.g. by an inhibition of spontaneous motor activity in mice on p.o. administration of from about 1 to about 100 mg/kg animal body weight of the compounds in accordance with the principles of Caviezel and Baillod [Pharm. Acta Helv. (1958), 33, 465–484]. Additionally, the compounds on administration to mice of from about 0.01 to about 30 mg/kg i.p. inhibit the hypermotility induced by 4,α-dimethyl-m-tyramine (H 77/77) in a test carried out according to the principles of J. B. Lassen, Psychopharmacologia 37, 331–340 (1974).

For the above mentioned use the dosage will, of course, vary depending on the compound employed, mode of administration and therapy desired. However, in general, satisfactory results are obtained with a daily dosage of from about 0.01 mg to about 100 mg per kg animal body weight, conveniently given in divided doses 2 to 4 times a day or in sustained release form. For the larger mammals, the total daily dosage is in the range from about 5 mg to about 100 mg, and dosage forms suitable for oral administration comprise from about 1 mg to about 50 mg of the compounds admixed with a solid or liquid pharmaceutical carrier or diluent.

The compounds of formula I are further useful as antidepressant agents as indicated in standard tests, for example, by an inhibition of tetrabenazine-induced catalepsy and ptosis in rats on intraperitoneal administration of from 5 to 15 mg per kilogram animal body weight of the compound in accordance with the method described by Stille (Arzneimittel-Forsch. 1964, 14, 534).

For the above-mentioned use the dosage will, of course vary depending on the compound employed, mode of administration and condition to be treated. However, in general satisfactory results are obtained with a daily dosage of from about 0.1 to about 15 mg per kg animal body weight, preferably given in divided doses 2 to 4 times a day, or in sustained release form. For the larger mammals the total daily dosage is in the range from about 5 to about 500 mg and dosage forms suitable for oral administration comprise from about 1.25 to about 250 mg of the compound admixed with a solid or liquid pharmaceutical carrier or diluent.

The compounds of formula I are further useful as sleep inducing agents, as indicated in standard tests. For example in one test according to the principles of H. Kleinlogel, European J. Pharmacol. 33, 159–163 (1975) an increase in the sleep phase II and a decrease of the wake phase is observed after administration to rats of from 2 to 80 mg/kg p.o. animal body weight of the compounds.

For the above mentioned use the dosage will, of course, vary depending on the compound employed, mode of administration and therapy desired. However, in general, satisfactory results are obtained with a daily dosage of from 0.1 mg to about 80 mg per kg animal body weight, conveniently given shortly before retiring to sleep. For the larger mammals, the total daily dosage is in the range from about 10 to about 100 mg.

The compounds of formula I may be administered in pharmaceutically acceptable acid addition salt form. Such acid addition salt forms exhibit the same order of activity as the free base forms. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

The neuroleptic activity is the preferred utility for compounds of formula I. The preferred compound is the Example 1 compound.

In one group of compounds $R_1$ is hydrogen, alkyl of 1 to 4 carbon atoms, hydroxyalkyl with a maximum of 4 carbon atoms, the hydroxy group of which may be acylated by an alkanoyl group of 2 to 18 carbon atoms, alkoxyalkyl with a maximum of 6 carbon atoms, cycloalkyl of 3 to 6 carbon atoms, cycloalkylalkyl of 4 to 7 carbon atoms or a group of formula II, wherein $R_6$ is hydrogen, halogen, or alkyl or alkoxy of 1 to 4 carbon atoms, and either (i) X is —$CH_2$— and n is 0, 1, 2 or 3 or (ii) X is —CO— and n is 1, 2 or 3, or (iii) X is —O— and n is 2 or 3, $R_2$ is hydrogen, halogen, trifluoromethyl or alkyl of 1 to 4 carbon atoms, $R_3$ is hydrogen, halogen, trifluoromethyl, or alkyl or alkoxy of 1 to 4 carbon atoms, $R_4$ is hydrogen, or alkyl or alkoxy of 1 to 4 carbon atoms and $R_5$ is hydrogen or alkyl of 1 to 4 carbon atoms, with the proviso that, when $R_2$ is hydrogen, $R_5$ is hydrogen.

In another group of compounds $R_1$ is hydrogen, alkyl, cycloalkylalkyl or a group of formula II, wherein $R_6$ is hydrogen or halogen, and X is —$CH_2$—, $R_2$ and $R_3$ independently are hydrogen or halogen, and $R_4$ and $R_5$ independently are hydrogen or alkyl with the proviso that when $R_2$ is hydrogen, then $R_5$ is hydrogen. Conveniently n is 1.

In a first group of compounds $R_1$ is hydrogen.
In a second group of compounds $R_1$ is alkyl.
In a third group of compounds $R_1$ is hydroxyalkyl.
In a fourth group of compounds $R_1$ is alkoxyalkyl.
In a fifth group of compounds $R_1$ is cycloalkyl.
In a sixth group of compounds $R_1$ is cycloalkylalkyl.

In a seventh group of compounds $R_1$ is a group of formula II.

In an eighth group of compounds X is —$CH_2$— and n is 0.

In a ninth group of compounds X is —$CH_2$— and n is 1.

In a tenth group of compounds X is —$CH_2$— and n is 2.

In an eleventh group of compounds X is —$CH_2$— and n is 3.

In a twelfth group of compounds X is —CO— and n is 1.

In a thirteenth group of compounds X is —CO— and n is 2.

In a fourteenth group of compounds X is —CO— and n is 3.

In a fifteenth group of compounds X is —O— and n is 2.

In a sixteenth group of compounds X is —O— and n is 3.

In a seventeenth group of compounds $R_2$ is hydrogen.
In an eighteenth group of compounds $R_2$ is halogen.
In a nineteenth group of compounds $R_2$ is trifluoromethyl.
In a twentieth group of compounds $R_2$ is alkyl.
In a twentyfirst group of compounds $R_3$ is hydrogen.
In a twentysecond group of compounds $R_3$ is halogen.
In a twentythird group of compounds $R_3$ is trifluoromethyl.
In a twentyfourth group of compounds $R_3$ is alkyl.
In a twentyfifth group of compounds $R_3$ is alkoxy.
In a twentysixth group of compounds $R_4$ is hydrogen.
In a twentyseventh group of compounds $R_4$ is alkyl.
In a twentyeighth group of compounds $R_4$ is alkoxy.
In a twentyninth group of compounds $R_5$ is hydrogen.
In a thirtieth group of compounds $R_5$ is alkyl.
In a thirtyfirst group of compounds $R_5$ is alkenyl.

What we claim is:

1. A compound of formula I,

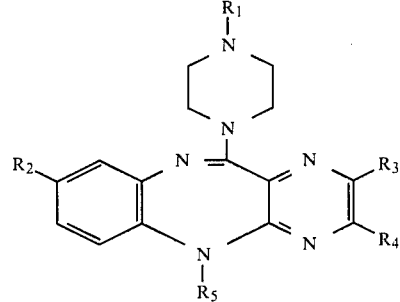

wherein
$R_1$ is hydrogen, alkyl of 1 to 4 carbon atoms, hydroxyalkyl with a maximum of 4 carbon atoms, the hydroxy group of which may be acylated by an alkanoyl group of 2 to 18 carbon atoms, alkoxyalkyl with a maximum of 6 carbon atoms, cycloalkyl of 3 to 6 carbon atoms, cycloalkylalkyl of 4 to 7 carbon atoms, or a group of formula II,

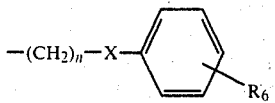

wherein
R₆ is hydrogen, halogen, or alkyl or alkoxy of 1 to 4 carbon atoms, and
either
(i) X is —CH₂— and n is 0, 1, 2 or 3 or
(ii) X is —CO— and n is 1, 2 or 3 or
(iii) X is —O— and n is 2 or 3,
$R_2$ is hydrogen, halogen, trifluoromethyl or alkyl of 1 to 4 carbon atoms,
$R_3$ is hydrogen, halogen, trifluoromethyl, or alkyl or alkoxy of 1 to 4 carbon atoms,
$R_4$ is hydrogen, or alkyl or alkoxy of 1 to 4 carbon atoms,
and
$R_5$ is hydrogen, alkyl of 1 to 4 carbon atoms or alkenyl of 3 or 4 carbon atoms, with the proviso that, when $R_2$ is hydrogen, $R_5$ is hydrogen,
said compound being in free base or in pharmaceutically acceptable acid addition salt form.

2. A compound of claim 1 wherein $R_1$ is hydrogen, alkyl of 1 to 4 carbon atoms, hydroxyalkyl with a maximum of 4 carbon atoms, the hydroxy group of which may be acylated by an alkanoyl group of 2 to 18 carbon atoms, alkoxyalkyl with a maximum of 6 carbon atoms, cycloalkyl of 3 to 6 carbon atoms, cycloalkylalkyl of 4 to 7 carbon atoms or a group of formula II, wherein R₆ is hydrogen, halogen, or alkyl or alkoxy of 1 to 4 carbon atoms, and either (i) X is —CH₂— and n is 0, 1, 2 or 3 or (ii) X is —CO— and n is 1, 2 or 3, or (iii) X is —O— and n is 2 or 3, $R_2$ is hydrogen, halogen, trifluoromethyl or alkyl of 1 to 4 carbon atoms, $R_3$ is hydrogen, halogen, trifluoromethyl, or alkyl or alkoxy of 1 to 4 carbon atoms, $R_4$ is hydrogen, or alkyl or alkoxy of 1 to 4 carbon atoms and $R_5$ is hydrogen or alkyl of 1 to 4 carbon atoms, with the proviso that, when $R_2$ is hydrogen, $R_5$ is hydrogen, said compound being in free base or in pharmaceutically acceptable acid addition salt form.

3. A compound of claim 1 wherein $R_1$ is hydrogen, alkyl of 1 to 4 carbon atoms, cycloalkylalkyl of 4 to 7 carbon atoms or a group of formula II, wherein R₆ is hydrogen or halogen, and X is —CH₂—, $R_2$ and $R_3$ independently are hydrogen or halogen, and $R_4$ and $R_5$ independently are hydrogen or alkyl of 1 to 4 carbon atoms, with the proviso that, when $R_2$ is hydrogen, then $R_5$ is hydrogen, said compound being in free base or in pharmaceutically acceptable acid addition salt form.

4. The compound of claim 1 wherein $R_1$, $R_2$, $R_3$, $R_4$ and $R_5$ respectively are CH₃, Cl, H, H and CH₃.

5. The compound of claim 1 wherein each of $R_1$, $R_2$, $R_3$, $R_4$ and $R_5$ is hydrogen.

6. The compound of claim 1 wherein $R_1$ is CH₂CH₂

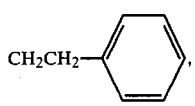

and each of $R_2$, $R_3$, $R_4$ and $R_5$ is hydrogen.

7. The compound of claim 1 wherein $R_1$ is CH₂CH₂

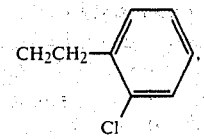

and each of $R_2$, $R_3$, $R_4$ and $R_5$ is hydrogen.

8. The compound of claim 1 wherein $R_1$ is CH₂

and each of $R_2$, $R_3$, $R_4$ and $R_5$ is hydrogen.

9. The compound of claim 1 wherein $R_1$, $R_2$, $R_3$, $R_4$ and $R_5$, respectively, are CH₃, H, Cl, H and H.

10. The compound of claim 1 wherein $R_1$, $R_2$, $R_3$, $R_4$ and $R_5$, respectively, are

CH₂CH₂—⌬,

H, Cl, H and H.

11. The compound of claim 1 wherein $R_1$, $R_2$, $R_3$, $R_4$ and $R_5$, respectively, are CH₂CH₂—⌬(Cl), H, Cl, H and H.

12. The compound of claim 1 wherein $R_1$, $R_2$, $R_3$, $R_4$ and $R_5$, respectively, are

CH₂—△,

H, Cl, H and H.

13. The compound of claim 1 wherein $R_1$ is CH₃, $R_2$ is Cl, and each of $R_3$, $R_4$ and $R_5$ is hydrogen.

14. The compound of claim 1 wherein $R_1$ is

CH₂CH₂—⌬, $R_2$ is Cl, and each of $R_3$, $R_4$ and $R_5$ is hydrogen.

15. The compound of claim 1 wherein $R_1$ is

CH₂—△, $R_2$ is Cl, and each of $R_3$, $R_4$ and $R_5$ is hydrogen.

16. The compound of claim 1 wherein $R_1$, $R_2$, $R_3$, $R_4$ and $R_5$, respectively, are CH₃, F, H, H and CH₃.

17. The compound of claim 1 wherein $R_1$, $R_2$, $R_3$, $R_4$ and $R_5$, respectively, are H, F, H, H and CH₃, said compound being in free base or in pharmaceutically acceptable acid addition salt form.

18. The compound of claim 1 wherein $R_1$, $R_2$, $R_3$, $R_4$ and $R_5$, respectively, are $CH_3$, Cl, Cl, H and H.

19. The compound of claim 1 wherein $R_1$ is $CH_3$, $R_2$ is F, and each of $R_3$, $R_4$ and $R_5$ is hydrogen.

20. The compound of claim 1 wherein $R_1$ is $CH_3$, and each of $R_2$, $R_3$, $R_4$ and $R_5$ is hydrogen.

21. The compound of claim 1 wherein $R_1$, $R_2$, $R_3$, $R_4$ and $R_5$, respectively, are H, Cl, H, H and $CH_3$, said compound being in free base or in pharmaceutically acceptable acid addition salt form.

22. The compound of claim 1 wherein $R_1$, $R_2$, $R_3$, $R_4$ and $R_5$, respectively, are $CH_3$, H, H, $CH_3$ and H, said compound being in free base or in pharmaceutically acceptable acid addition salt form.

23. The compound of claim 1 wherein $R_1$, $R_2$, $R_3$, $R_4$ and $R_5$, respectively, are $CH_3$, Cl, H, $CH_3$ and H, said compound being in free base or in pharmaceutically acceptable acid addition salt form.

24. The compound of claim 1 wherein $R_1$, $R_2$, $R_3$, $R_4$ and $R_5$, respectively, are $CH_3$, Cl, Cl, $CH_3$ and H.

25. The compound of claim 1 wherein $R_1$ is $CH_3$, $R_2$ is Br, and each of $R_3$, $R_4$ and $R_5$ is hydrogen.

* * * * *

UNITED STATES PATENT AND TRADEMARK OFFICE
CERTIFICATE OF CORRECTION

PATENT NO. : 4,337,198
DATED : June 29, 1982
INVENTOR(S) : DIETER SORG, ET AL.

It is certified that error appears in the above-identified patent and that said Letters Patent is hereby corrected as shown below:

Column 9, line 58; after "is", delete "$CH_2CH_2$".
Column 9, line 67; after "is", delete "$CH_2CH_2$".
Column 10, line 10; after "is", delete "$CH_2$".

Signed and Sealed this

Twenty-ninth Day of March 1983

[SEAL]

Attest:

GERALD J. MOSSINGHOFF

Attesting Officer     Commissioner of Patents and Trademarks